(12) United States Patent
Sundar

(10) Patent No.: US 7,105,198 B2
(45) Date of Patent: Sep. 12, 2006

(54) METHOD FOR COATING STENT

(75) Inventor: Rangarajan Sundar, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 154 days.

(21) Appl. No.: 10/050,219

(22) Filed: Jan. 14, 2002

(65) Prior Publication Data
US 2003/0135255 A1 Jul. 17, 2003

(51) Int. Cl.
*B05D 3/12* (2006.01)
(52) U.S. Cl. ................... 427/2.24; 427/430.1
(58) Field of Classification Search ......... 427/2.24, 427/2.25, 2.27, 430.1, 443.2
See application file for complete search history.

(56) References Cited

U.S. PATENT DOCUMENTS

| 5,234,457 | A | * | 8/1993 | Andersen ............ 606/198 |
|---|---|---|---|---|
| 5,464,650 | A | * | 11/1995 | Berg et al. .............. 427/2.3 |
| 5,837,313 | A | * | 11/1998 | Ding et al. ............ 427/2.21 |
| 5,891,507 | A | * | 4/1999 | Jayaraman ............ 427/2.25 |
| 5,935,162 | A | | 8/1999 | Dang |
| 6,120,847 | A | | 9/2000 | Yang et al. |
| 6,156,373 | A | | 12/2000 | Zhong et al. |
| 6,159,229 | A | | 12/2000 | Jendersee et al. |
| 6,284,305 | B1 | * | 9/2001 | Ding et al. ............ 427/2.28 |
| 6,358,556 | B1 | * | 3/2002 | Ding et al. ............ 427/2.24 |
| 6,399,144 | B1 | * | 6/2002 | Dinh et al. ............ 427/2.24 |
| 6,555,157 | B1 | * | 4/2003 | Hossainy ............ 427/2.24 |
| 6,783,793 | B1 | * | 8/2004 | Hossainy et al. ....... 427/2.25 |

FOREIGN PATENT DOCUMENTS

WO  WO 01/52772  * 7/2001

* cited by examiner

*Primary Examiner*—Erma Cameron

(57) ABSTRACT

A method of coating a stent includes immersing a portion of the stent into a coating liquid, and withdrawing the immersed portion of the stent from the coating liquid. The stent is simultaneously rotated with respect to the coating liquid while the stent is being immersed and withdrawn.

10 Claims, 4 Drawing Sheets

METHOD FOR COATING STENT

TECHNICAL FIELD OF THE INVENTION

The present invention relates generally to the field of implantable medical devices. More particularly, the invention relates to a stent delivery system and device having a coating, and a method for coating the same.

BACKGROUND OF THE INVENTION

Balloon angioplasty has been used for the treatment of narrowed and occluded blood vessels. A frequent complication associated with the procedure is restenosis, or vessel re-narrowing. Within 3–6 months of angioplasty, restenosis occurs in almost 50 percent of patients. In order to reduce the incidence of re-narrowing, several strategies have been developed. Implantable devices, such as stents, have been used to reduce the rate of angioplasty related restenosis by about half. The use of such devices has greatly improved the prognosis of these patients. Nevertheless, restenosis remains a formidable problem associated with the treatment of narrowed blood vessels.

Restenosis associated with interventional procedures such as balloon angioplasty may occur by two mechanisms: thrombosis and intimal hyperplasia. During angioplasty, a balloon is inflated within an affected vessel thereby compressing the blockage and imparting a significant force, and subsequent trauma, upon the vessel wall. The natural antithrombogenic lining of the vessel lumen may become damaged thereby exposing thrombogenic cellular components, such as matrix proteins. The cellular components, along with the generally antithrombogenic nature of any implanted materials (e.g., a stent), may lead to the formation of a thrombus, or blood clot. The risk of thrombosis is generally greatest immediately after the angioplasty.

The second mechanism of restenosis is intimal hyperplasia, or excessive tissue re-growth. The trauma imparted upon the vessel wall from the angioplasty is generally believed to be an important factor contributing to hyperplasia. This exuberant cellular growth may lead to vessel "scarring" and significant restenosis. The risk of hyperplasia associated restenosis is usually greatest 3 to 6 months after the procedure.

Prosthetic devices, such as stents or grafts, may be implanted during interventional procedures such as balloon angioplasty to reduce the incidence of vessel restenosis. To improve device effectiveness, stents may be coated with one or more therapeutic agents providing a mode of localized drug delivery. The therapeutic agents are typically intended to limit or prevent the aforementioned mechanisms of restenosis. For example, antithrombogenic agents such as heparin or clotting cascade IIb/IIIa inhibitors (e.g., abciximab and eptifibatide) may be coated on the stent thereby diminishing thrombus formation. Such agents may effectively limit clot formation at or near the implanted device. Some antithrombogenic agents, however, may not be effective against intimal hyperplasia. Therefore, the stent may also be coated with antiproliferative agents or other compounds to reduce excessive endothelial re-growth. Therapeutic agents provided as coatings on implantable medical devices may effectively limit restenosis and reduce the need for repeated treatments.

Several considerations should be made when devising a strategy for coating implantable prosthetic devices, such as stents or grafts. One consideration in coating strategy relates to surface uniformity. Ideally, coatings should be evenly applied with limited surface imperfections. Some coating strategies, however, may produce pooling of the coating material and/or dry spots. Failure to control surface uniformity may lead to inaccurate, non-uniform drug dose delivery and therapeutic variability from device to device. Therefore, it would be desirable to provide a uniform stent coating.

Another consideration in coating strategy relates to topography. It may be desirable for the coating to be disposed on certain areas of the stent. For example, stents typically have a wire mesh with open spaces formed between. Some coating strategies may leave 'bridged' material within the open spaces. Such coating bridges may break off causing complications or may prevent the device from expanding or functioning properly. As another example, only certain portions of the stent may require coating, or several coating layers may be required. As such, it would be desirable to control the stent coating topography.

Another consideration in coating strategy relates to efficiency. It may be desirable to effectively coat the implantable device in relatively short time, with a minimal amount of coating material. Some coating strategies require lengthy steps, thereby reducing the amount of devices that can be coating within a certain period. In addition, some strategies do not utilize coating material in a complete manner thereby increasing cost. For example, coating material that is vaporized may get dispersed on areas other than the stent surface. Therefore, it would be desirable to efficiently coat the stent.

Accordingly, it would be desirable to provide a strategy for coating a stent that would overcome the aforementioned and other disadvantages.

SUMMARY OF THE INVENTION

One aspect of the present invention provides a stent delivery system. The system includes a catheter, a balloon operably attached to the catheter, and a stent disposed on the balloon. The stent includes at least one coating applied by dipping a portion of the stent into a coating liquid while simultaneously rotating the stent. The coating may include a therapeutic agent and may be substantially on an outer surface of the stent. The coating may be about 1 to 150 microns thick. The stent may be dipped at a rate of about 0.1 to 25.0 millimeters per second, and for a time period of about 5 seconds to 10 minutes. The stent may be rotated at a rate of about 100 to 25,000 rotations per minute. The system may further include a control sequence, and a programmable logic chip. The logic chip may control at least one of the dipping and rotation of the stent based on the control sequence.

Another aspect of the invention provides a stent device. The stent device includes a body, and at least one coating rotationally applied to a portion of the body, while the body is at least partially immersed in a coating liquid. The coating may include a therapeutic agent and may be substantially on an outer surface of the body. The coating may be about 1 to 150 microns thick. The body may be dipped at a rate of about 0.1 to 25.0 millimeters per second, and for a time period of about 5 seconds to 10 minutes. The body may be rotated at a rate of about 100 to 25,000 rotations per minute. The device may further include a control sequence, and a programmable logic chip. The logic chip may control the rotational application based on the control sequence.

Another aspect of the invention provides a method for coating a stent. The method includes immersing a portion of the stent into a coating liquid, and withdrawing the immersed portion of the stent from the coating liquid. The method further includes simultaneously rotating the stent with respect to the coating liquid while the stent is being immersed and withdrawn. The rotation may force the coating liquid to an outer portion of the stent. Multiple layered coatings may be applied. Immersing the stent may include controlling a stent wetting characteristic. The stent may be immersed at a rate of about 0.1 to 25.0 millimeters per second, and for a time period of about 5 seconds to 10 minutes. The stent may be rotated at a rate of about 100 to 3,500 rotations per minute during immersion. Withdrawing the stent may include controlling a stent coating thickness, wherein the coating may be about 1 to 150 microns thick. The stent may be withdrawn at a rate of about 0.1 to 25.0 millimeters per second, and rotated at a rate of about 600 to 25,000 rotations per minute. The method may further include programming a control sequence, and controlling at least one of the immersion, withdrawal, and rotation based on the control sequence.

Another aspect of the invention provides a stent device. The stent devices includes means for immersing a portion of the stent into a coating liquid, and means for withdrawing the immersed portion of the stent from the coating liquid. The stent device further includes means for simultaneously rotating the stent with respect to the coating liquid while the stent is being immersed and withdrawn. The stent device may further include a control sequence, and means for controlling at least one of the immersion, withdrawal, and rotation based on the control sequence.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PRESENTLY PREFERRED EMBODIMENTS

Figure 1:
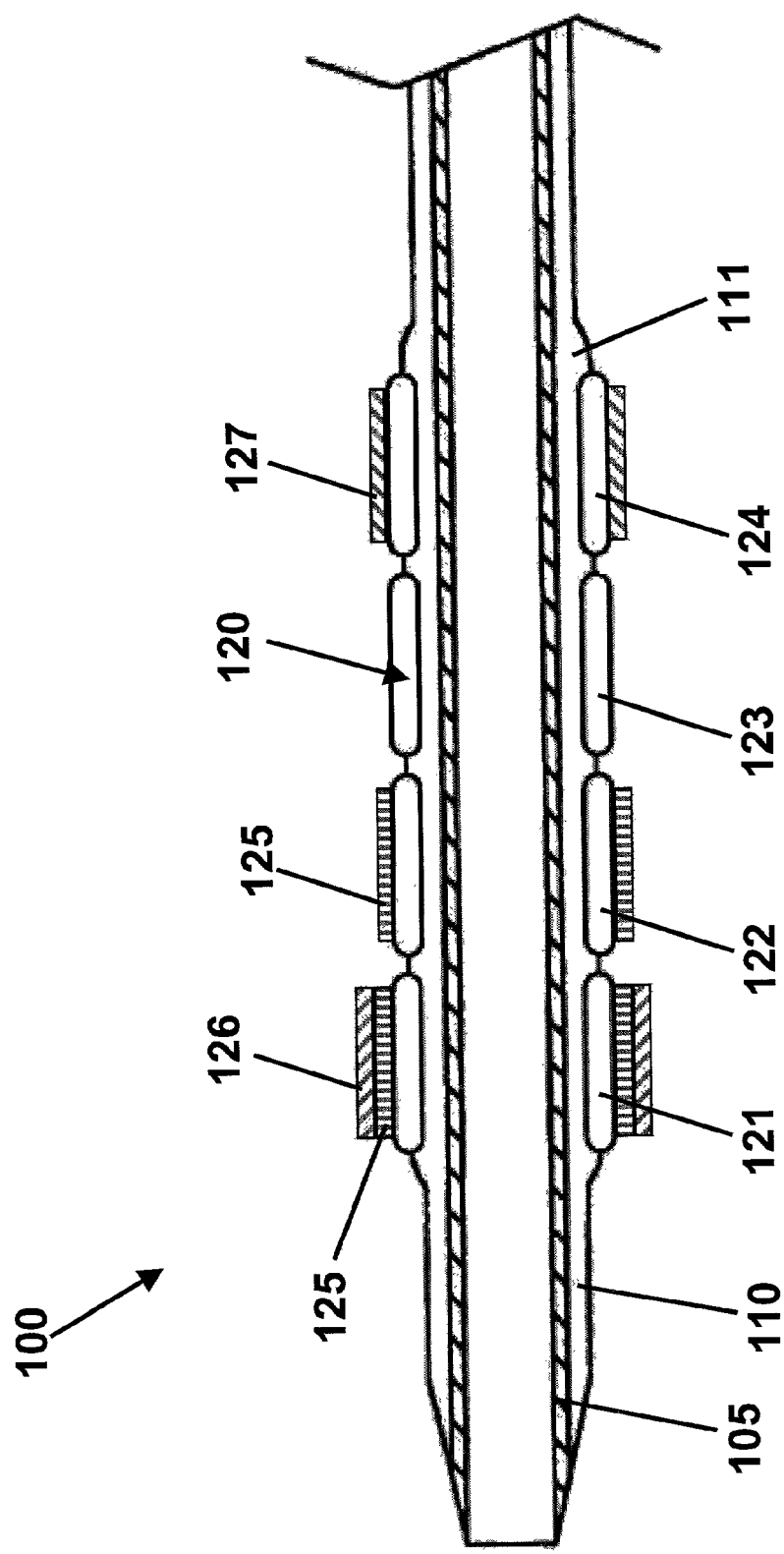
FIG. 1 is a perspective view of a stent delivery system made in accordance with the present invention.

Referring to the drawings, wherein like reference numerals refer to like elements, FIG. 1 is a perspective view of a stent delivery system made in accordance with the present invention and shown generally by numeral 100. The stent delivery system 100 includes a catheter 105, a balloon 110 operably attached to the catheter 105, and a stent 120 disposed on the balloon 110. The balloon 110, shown in a collapsed state, may be any variety of balloons capable of expanding the stent 120. The balloon 110 may be manufactured from any sufficiently elastic material such as polyethylene, polyethylene terephthalate (PET), nylon, or the like. In one embodiment, the balloon 110 may include retention means 111, such as mechanical or adhesive structures, for retaining the stent 120 until it is deployed. The catheter 105 may be any variety of balloon catheters, such as a PTCA balloon catheter, capable of supporting a balloon during angioplasty.

The stent 120 may be any variety of implantable prosthetic devices capable of carrying a coating known in the art. In one embodiment, the stent 120 may have a plurality of identical cylindrical stent segments placed end to end. Four stent segments 121, 122, 123, and 124 are shown, and it will be recognized by those skilled in the art that an alternate number of stent segments may be used. The stent 120 includes at least one coating applied dipping a portion of the stent 120 into a coating liquid while simultaneously rotating the stent 120. In one embodiment, three coating layers 125, 126, and 127 may be applied by a dip-spin coating process on various segments 121, 122, and 124. Segment 121 is shown having two coating layers 125, and 126. Segment 122 and segment 124 are shown each having one coating layer 125, and 127, respectively. Segment 123 is shown having no coating. The coating layers 125, 126, and 127 are merely exemplary, and it should be recognized that other coating configurations are possible.

Figure 2:
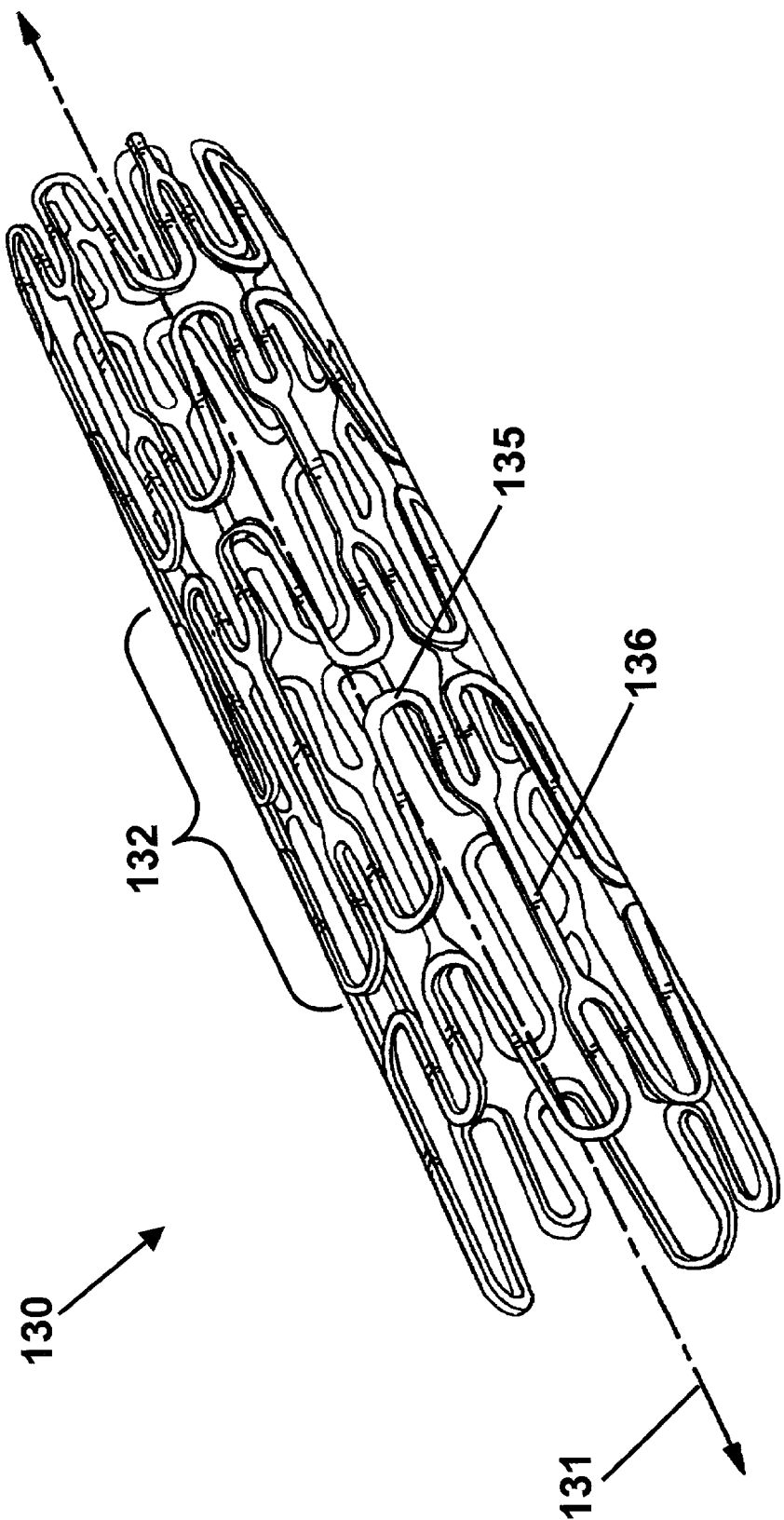
FIG. 2 is a perspective view of a prior art stent compatible with the disclosed coating process of the present invention.

To describe the dip-spin coating process of the present invention, the following figures and description are provided. FIG. 2 is a perspective view of a prior art stent 130 compatible with the coating process of the present invention. Those skilled in the art will recognize that numerous stents, grafts, and implantable prosthetic devices are compatible with the disclosed coating method and that the described stent 130 example is merely one illustration of the process. The stent 130 is an example of a wire-tubular hybrid stent disclosed by U.S. Pat. No. 5,935,162 issued to Dang.

The stent 130 includes a generally tubular body defining a passageway extending along a longitudinal axis 131. The stent 130 is formed from a plurality of cylindrical segments 132 arranged successively along the longitudinal axis 131. Each of cylindrical segments 132 has a length along the longitudinal axis 131 and includes a plurality of W-shaped elements 135. The W-shaped elements 135 open in alternating directions along the longitudinal axis 131 about the perimeter or circumference of the cylindrical segments 132. The W-shaped elements 135 are connected to each other by a tie member 136 that is attached to center sections of each of the W-shaped elements 135.

The stent 130 is shown in an expanded state in which the cylindrical segments 132 have been expanded radially outward from the longitudinal axis 131. The stent 130 may be compressed into a smaller diameter for delivery within a vessel lumen at which point the stent 130 may be expanded to provide support to the vessel. The stent 130 may be of the self-expanding variety and manufactured from nickel titanium alloys and other alloys that exhibit superlastic behavior (i.e., capable of significant distortion without plastic deformation). Alternatively, the stent 130 may be designed to be expanded by a balloon or some other device, and may be manufactured from an inert, biocompatible material with high corrosion resistance. The biocompatible material should ideally be plastically deformed at low-moderate stress levels. Suitable materials include, but are not limited to, tantalum, MP35N, stainless steel, titanium ASTM F63-83 Grade 1, niobium or high carat gold K 19-22.

Figure 3:
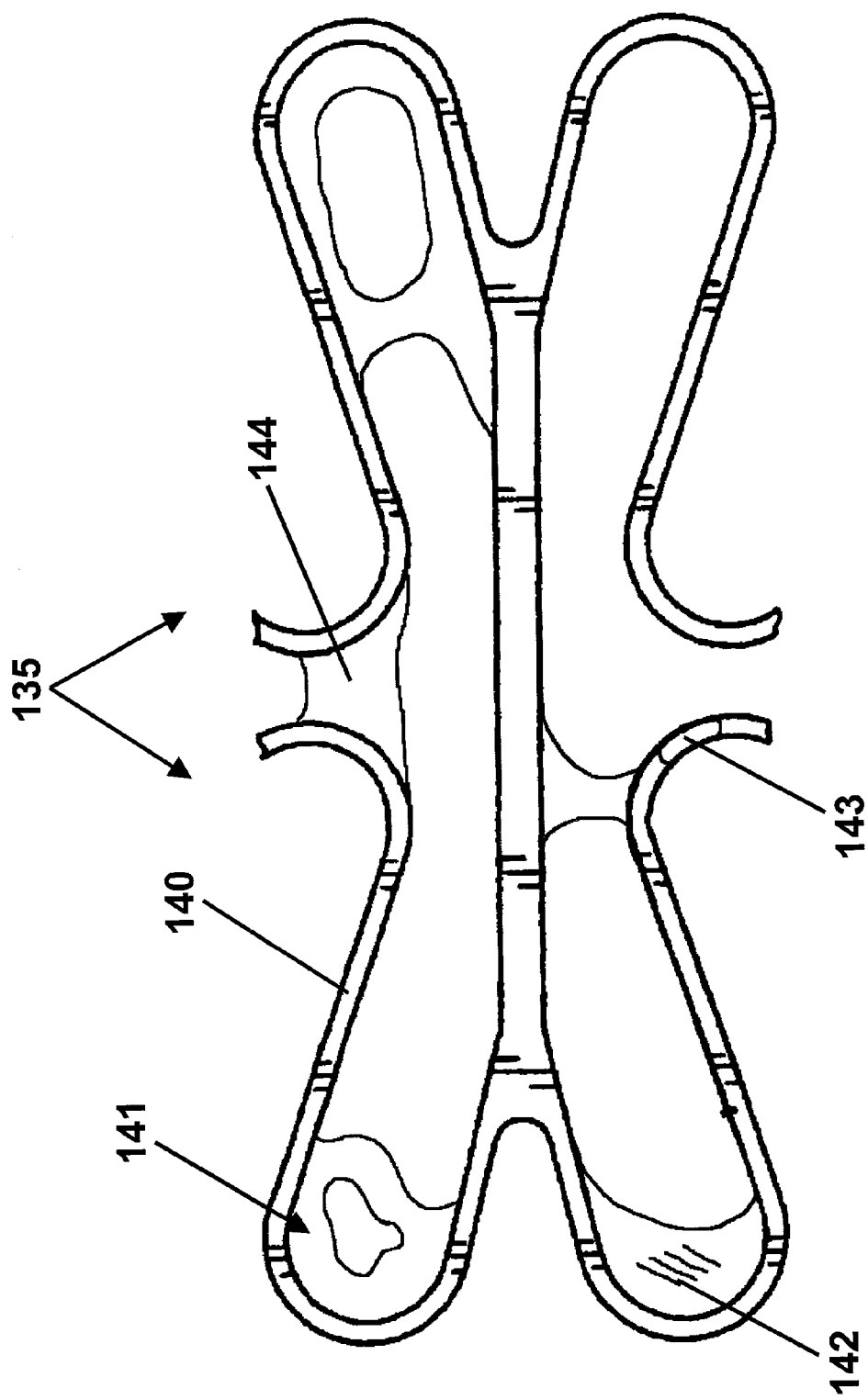
FIG. 3 is a magnified view of two W-shaped elements of the stent in FIG. 2.

FIG. 3 is a magnified view of two W-shaped elements 135 of the stent 130 in FIG. 1. The surface of the W-shaped elements is shown with a polymeric coating 140 having coating anomalies 141. The anomalies 141 may take on numerous configurations, but common examples include pooling 142, dry spots 143, and bridging 144. The anomalies 141 are typically produced during an imperfect coating process. Ideally, a coating process should produce an even coating 140 free of pooling 142, dry spots 143, and bridging 144. Such coating anomalies 141 may lead to inaccurate, non-uniform drug dose delivery and therapeutic variability. In addition, anomalies such as bridging 144 may break off causing complications or may prevent the stent 130 from expanding or functioning properly. For example, bridging 144 materials may enter the bloodstream thereby releasing therapeutic agents in undesired locations. Accordingly, it is desirable to minimize coating anomalies 141.

Figure 4:
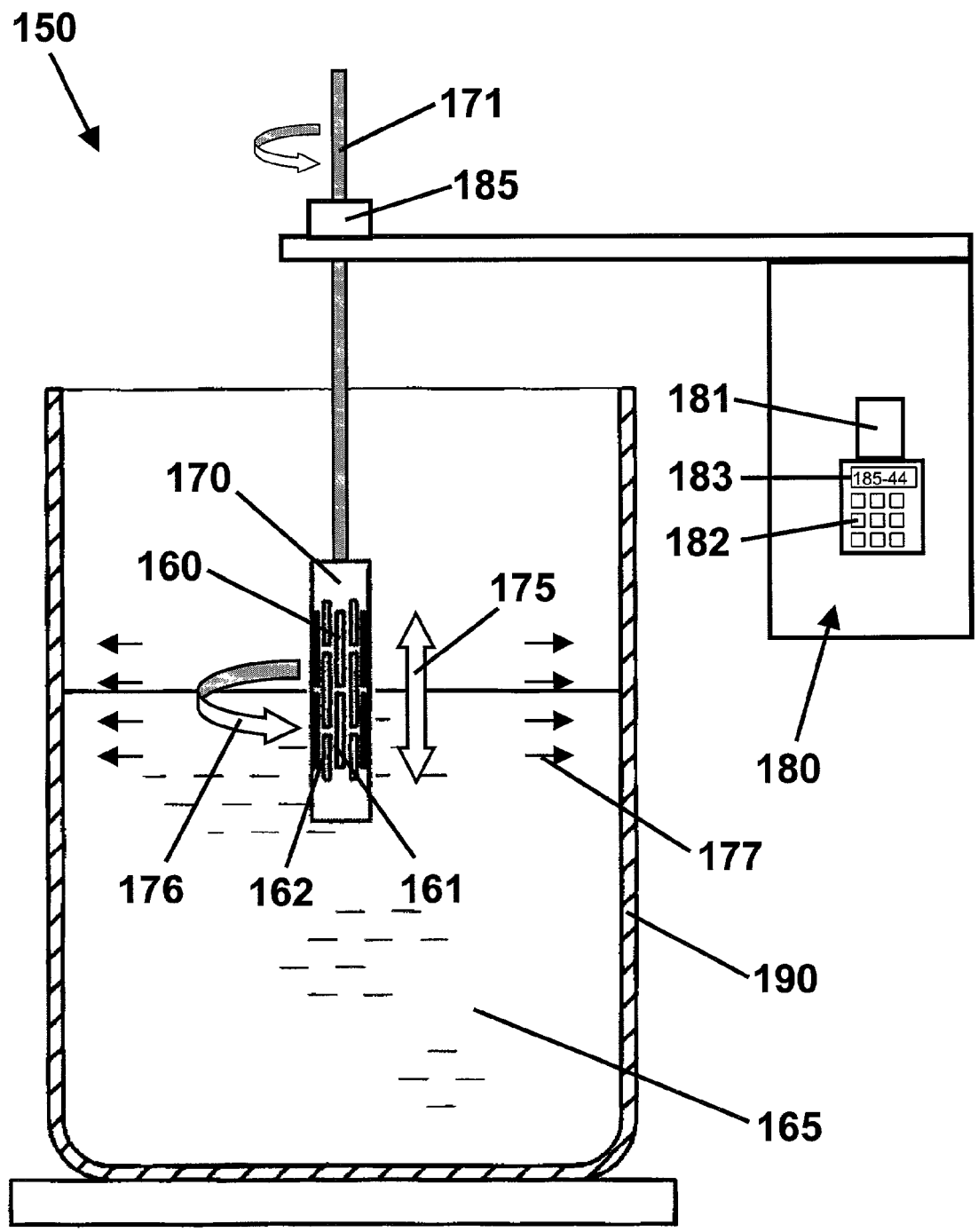
FIG. 4 is diagram of a stent coating process made in accordance with the present invention.

Turning now to FIG. 4, a stent coating process made in accordance with the present invention is shown generally as numeral 150. The coating process 150 provides one or more coatings on a portion of a stent device 160. A stent device 160, referred herein as "stent", may be any number of implantable prosthetic devices capable of carrying a coating. The stent 160 may include a body 161 and at least one coating 162 rotationally applied to a portion of the body 161, while the body 161 is at least partially immersed in a coating liquid 165. The stent 160 may be manufactured from a skeletal framework or mesh of material forming a tube-like structure and may be capable of self-expanding or being expanded by another device such as a balloon. The stent 160 material may include any number of metallic and polymeric biocompatible materials recognized in the art for such devices.

To apply the coating 162, the stent 160 may be slidably mounted on a cylindrically shaped mandrel 170 that is fixably attached to a rod 171. The stent 160, mandrel 170, and rod 171, may be moved during the coating process 150 by an actuator 180. The actuator 180 may provide vertical 175 (e.g., immersion and withdrawal) and rotational 176 movements. The actuator 180 may include a logic chip 181 programmed with a control sequence to control timing, speed, directionality, and variations of the vertical 175 and rotational 176 movement characteristics. The actuator 180 may further include a keypad 182 and display 183 for modifying and viewing portions of the control sequence, respectively. The control sequence and corresponding movement characteristics may be actuated by one or more motors 185 controlled by the logic chip 181. The motors 185 may be of any variety of electric motors, hydraulic units, and the like, recognized in the art for providing rotational and liner movements.

The stent 160 may be dipped in the coating liquid 165 carried within a compatible container 190 (i.e., inert with respect to the coating liquid 165). In one embodiment, the coating liquid 165 may be a polymeric solution. The polymeric solution may include one or more polymers, solvents, and therapeutic agents. The polymer may be dissolved in an appropriate solvent to provide a matrix for incorporating the therapeutic agent within the coating. Suitable polymers include, but are not limited to, urethane, polycaprolactone (PCL), polymethylmethacrylate (PMMA), and the like. Suitable solvents include, but are not limited to, acetone, ethyl acetate, tetrahydrofuran (THF), chloroform, N-methylpyrrolidone (NMP), and the like. Suitable therapeutic agents include, but are not limited to, antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents, agents having a desirable therapeutic application, and the like. Specific example of therapeutic agents include abciximab, angiopeptin, colchicine, eptifibatide, heparin, hirudin, lovastatin, methotrexate, streptokinase, taxol, ticlopidine, tissue plasminogen activator, trapidil, urokinase, and growth factors VEGF, TGF-beta, IGF, PDGF, and FGF.

The stent coating process 150 may begin by preparing the coating liquid 165, such as a polymeric solution. In one embodiment, preparation of the polymeric solution may include dissolving polymer in solvent. The choice of solvent controls the ability to place the polymer into solution and, thus, should be considered. The use of solvent blends may also be considered. A blend of solvents may be preferred to ensure uniform coating 162 with a smooth surface. Solvent volatility may also be considered. Too rapid solvent evaporation may result in surface imperfections; too slow solvent evaporation may result in handling defects as well as high solvent retention. As such, the polymer-solvent solution should ideally provide a uniform coating 162, smooth surface without major imperfections, and little to no solvent retention. In one embodiment, the polymer-solvent solution may have a solids range from about 1 to 10 percent and a viscosity of about 5 to 30 centipoises.

One or more therapeutic agents may be added to the polymeric solution. Ideally, the polymer-solvent solution should be capable of dispersing the agent evenly throughout the solution. Furthermore, the polymer-solvent solution should not chemically alter the therapeutic character of the agent. Examples of suitable polymer/solvent/therapeutic agent combinations include: polylactic acid/trichloroethane/colchicines; polyurethane/THF/taxol; (poly(D,L-lactide)/PCL)/dimethylformamide/hirudin; (poly(D,L-lactide)/polygycolide)/ethylacetate/ticlopidine; and polyethylene oxide/ethanol/heparin. These combinations are merely exemplary, and it should be recognized that other combinations are possible.

After the polymer and therapeutic agent have been dissolved in the solvent, the polymeric solution may be aged and cleared. In one embodiment, the solution may be mixed for 12 or more hours while being stirred to ensure complete dissolution and homogeneity. The solution may also be filtered with an appropriate filter to remove any impurities and haziness. Those skilled in the art will recognize that the preparation of the coating liquid 165 may vary greatly and may be contingent upon the materials used. After the coating liquid 165 has been prepared, it may be transferred to the container 190.

The stent 160 mounted on the mandrel 170 may begin rotation as effected by the actuator motor 185. The stent 160 may be rotated initially at a rate of about 100 to 3,500 rotations per minute (rpm). More preferably, the stent 160 may be rotated at about 500 to 700 rpm. The stent 160 may then be immersed in the coating liquid 165 at a rate of about 0.1 to 25.0 millimeters per second (mm/sec). More preferably, the stent 160 may be immersed at a rate of about 0.5 to 5.0 millimeters per second. The immersion may continue until the stent body 161 portion requiring coating has been immersed. The stent 160 may be immersed for a total time of about 5 seconds to 10 minutes. More preferably, the stent 160 may be immersed for about 5 to 20 seconds. The immersion time may control a stent wetting characteristic; the characteristic relating to how completely the stent is covered with the coating liquid 165. Ideally, the stent 160 should be evenly "wetted" free from any dry spots. A lower viscosity coating liquid 165 generally require shorter immersion time. The temperature of the coating liquid 165 affects its viscosity and, therefore, may also be a factor in determining immersion time.

Once the stent 160 has been immersed, the stent 160 may begin withdrawal wherein it is rotated at about 600 to 25,000 rpm. More preferably, the stent 160 may be rotated during withdrawal at a rate of about 3,000 to 10,000 rpm. The rate of rotation during withdrawal may influence the uniformity of the coating 162. For example, too slow rotation during withdrawal may lead to coating pooling; too fast rotation may excessively remove coating material. The stent 160 may be withdrawn at a rate of about 0.1 to 25.0 mm/sec. More preferably, the stent 160 may be withdrawn initially at 0.1 mm/sec and then at 0.7 mm/sec providing a uniform coating 162. The withdrawal rate may control a coating thickness. Generally, faster withdrawal rates produce greater coating thickness. The coating 162 may be in the range of about 1 to 150 microns thick. More preferably, the coating 162 may be about 5 to 30 microns thick. The rotating stent 160 may experience a significant centrifugal force 177. The coating liquid 165 may be forced substantially from an inner to an outer surface portion of the stent 160. As a result, the bulk of the coating 162 and integral therapeutic agent may be positioned proximate to where the stent 160 contacts the vessel wall. This topography may provide efficient coating liquid 165 utilization and an effective drug delivery method.

Another factor affecting the coating process 150 pertains to the manner in which the coated stent 160 is dried. Ideally, the coated stent 160 should be dried to allow for a desirable rate of solvent evaporation. For example, too rapid drying causes moisture to be entrained in the coating 162 causing surface blemishes; too slow drying increases solvent retention. The drying conditions may vary greatly and are generally dependant upon the nature of the coating liquid 165 and, to a great extent, the solvent used. After the coating 162 has dried, the stent coating process 150 may be repeated to provide additional coating(s) positioned on top of, or on other locations of the stent 160.

The described stent coating process 150 may provide a coating 162 that is controllable, uniform, efficient, and free from bridging and pooling anomalies. The process 150 may be optimized by customizing the timing, speed, directionality, and variations of the vertical 61 and rotational 62 movement characteristics. These characteristics may be adjusted based on the nature of the stent 160 and coating liquid 165 used. The concurrent spinning and dipping of the stent 160 may speed the rate at which the coating 162 is applied. In addition, the process 150 may provide efficient utilization of coating liquid 165. Accordingly, the process 150 may reduce the time and cost of conventional coating strategies.

While the embodiments of the invention disclosed herein are presently considered to be preferred, various changes and modifications can be made without departing from the spirit and scope of the invention. For example, the stent configuration is not limited to any particular stent design. In addition, the coating liquid composition and coating process movement characteristics may be varied considerably while providing a desirable coating. Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

The invention claimed is:

1. A method for coating a stent comprising:
    immersing a portion of the stent into a coating liquid while rotating the stent around its longitudinal axis at a rate of about 100 to 3.500 rotations per minute; and
    withdrawing the immersed portion of the stent from the coating liquid while rotating the stent around its longitudinal axis at a rate of about 600 to 25.000 rotations per minute.

2. The method of claim 1 wherein the rotation forces the coating liquid to an outer portion of the stent.

3. The method of claim 1 further comprising applying multiple layered coatings.

4. The method of claim 1 wherein immersing the stent comprises controlling a stent wetting characteristic.

5. The method of claim 1 wherein the stent is immersed at a rate of about 0.1 to 25.0 millimeters per second.

6. The method of claim 1 wherein the stent is immersed for a time period of about 5 seconds to 10 minutes.

7. The method of claim 1 wherein withdrawing the stent comprises controlling a stent coating thickness.

8. The method of claim 7 wherein the stent coating thickness comprises a thickness of about 1 to 150 microns.

9. The method of claim 1 wherein the stent is withdrawn at a rate of about 0.1 to 25.0 millimeters per second.

10. The method of claim 1 further comprising:
    programming a control sequence; and
    controlling at least one of the immersion, withdrawal, and rotation based on the control sequence.

* * * * *